(12) United States Patent
Matsumura et al.

(10) Patent No.: US 11,246,830 B2
(45) Date of Patent: Feb. 15, 2022

(54) EMULSIFIED GEL COMPOSITION

(71) Applicant: HISAMITSU PHARMACEUTICAL CO., INC., Tosu (JP)

(72) Inventors: Shinya Matsumura, Tosu (JP); Toshihiro Nakanishi, Tosu (JP); Yasuhisa Kose, Tosu (JP)

(73) Assignee: HISAMITSU PHARMACEUTICAL CO., INC., Tosu (JP)

( * ) Notice: Subject to any disclaimer, the term of this patent is extended or adjusted under 35 U.S.C. 154(b) by 0 days.

(21) Appl. No.: 16/975,161

(22) PCT Filed: Feb. 19, 2019

(86) PCT No.: PCT/JP2019/006125
§ 371 (c)(1),
(2) Date: Aug. 24, 2020

(87) PCT Pub. No.: WO2019/167727
PCT Pub. Date: Sep. 6, 2019

(65) Prior Publication Data
US 2020/0397694 A1    Dec. 24, 2020

(30) Foreign Application Priority Data
Feb. 27, 2018  (JP) .............................. JP2018-033218

(51) Int. Cl.
*A61K 9/06* (2006.01)
*A61K 9/107* (2006.01)
(Continued)

(52) U.S. Cl.
CPC ................ *A61K 9/06* (2013.01); *A61K 9/107* (2013.01); *A61K 31/196* (2013.01); *A61K 47/10* (2013.01);
(Continued)

(58) Field of Classification Search
None
See application file for complete search history.

(56) References Cited

U.S. PATENT DOCUMENTS 6,075,056 A * 6/2000 Quigley, Jr. ........... A61K 31/57
514/649
2004/0101538 A1  5/2004 Larnier et al.
(Continued)

FOREIGN PATENT DOCUMENTS

EP    3037088 A1   6/2016
JP    6456622 A    3/1989
(Continued)

OTHER PUBLICATIONS

International Preliminary Report on Patentability with Translation of Written Opinion of the International Searching Authority dated Sep. 3, 2020 in International Application No. PCT/JP2019/006125.
(Continued)

*Primary Examiner* — Melissa S Mercier
(74) *Attorney, Agent, or Firm* — Sughrue Mion, PLLC

(57) ABSTRACT

The present invention provides an emulsified gel composition comprising a physiologically active substance, water, a gelling agent, an anti-peeling agent, and a surfactant having an HLB value of 18 to 20, in which the gelling agent is a nonionic water-soluble polymer, and the anti-peeling agent is one or more compounds selected from the group consisting of sucrose, sorbitol, polyethylene glycol, glycerin, a (meth)acrylic-based polymer compound, and a polyoxyethylene hydrogenated castor oil.

11 Claims, 3 Drawing Sheets

(51) Int. Cl.
*A61K 31/196* (2006.01)
*A61K 47/32* (2006.01)
*A61K 47/38* (2006.01)
*A61K 47/10* (2017.01)
*A61K 47/44* (2017.01)

(52) U.S. Cl.
CPC .............. *A61K 47/32* (2013.01); *A61K 47/38* (2013.01); *A61K 47/44* (2013.01)

(56) References Cited

U.S. PATENT DOCUMENTS

| | | |
|---|---|---|
| 2010/0099766 A1 | 4/2010 | Zhang et al. |
| 2016/0175262 A1 | 6/2016 | Tsurushima et al. |

FOREIGN PATENT DOCUMENTS

| | | | |
|---|---|---|---|
| JP | 249722 A | 2/1990 | |
| JP | 912452 A | 1/1997 | |
| JP | 10-175832 A | 6/1998 | |
| JP | 10182450 A | 7/1998 | |
| JP | 2000-161514 A | 7/2000 | |
| JP | 2001342113 A | 12/2001 | |
| JP | 2002-3354 A | 1/2002 | |
| JP | 2005-47908 A | 2/2005 | |
| JP | 2006-151836 A | 6/2006 | |
| JP | 2006328015 A | 12/2006 | |
| JP | 2007-126415 A | 5/2007 | |
| JP | 2013-512917 A | 4/2013 | |
| WO | 92/07561 A1 | 5/1992 | |
| WO | 02/078648 A2 | 10/2002 | |
| WO | 2011/068955 A1 | 6/2011 | |
| WO | 2014/017411 A1 | 1/2014 | |
| WO | 2016/038553 A1 | 3/2016 | |

OTHER PUBLICATIONS

International Search Report dated Apr. 23, 2019 from the International Searching Authority in International Application No. PCT/JP2019/006125.

Communication dated Oct. 21, 2021 from the European Patent Office in application No. 19761141.1.

Communication dated Dec. 22, 2021 from the European Patent Office in application No. 19761705.3.

* cited by examiner

EMULSIFIED GEL COMPOSITION

CROSS REFERENCE TO RELATED APPLICATIONS

This application is a National Stage of International Application No. PCT/JP2019/006125, filed Feb. 19, 2019, claiming priority to Japanese Patent Application No. 2018-033218, filed Feb. 27, 2018.

TECHNICAL FIELD

The present invention relates to an emulsified gel composition.

BACKGROUND ART

As a dosage form of a transdermal formulation, a patch, a poultice, a tape, an ointment, a gel, a lotion, a cream, an aerosol and the like are known. When a composition having high liquidity among these, such as a lotion, is applied onto the skin, the applied composition may flow down in some cases. On the other hand, a gel comprises a gelling agent in its composition, and the viscosity of the composition is increased, and therefore, even after application onto the skin, the composition is difficult to flow down. Patent Literatures 1 to 5 report a gel comprising a physiologically active substance such as diclofenac or a salt thereof.

CITATION LIST

Patent Literature

Patent Literature 1: JP H2-49722 A
Patent Literature 2: JP H10-182450 A
Patent Literature 3: JP S64-56622 A
Patent Literature 4: JP 2006-328015 A
Patent Literature 5: WO 92/07561 A1

SUMMARY OF INVENTION

Technical Problem

In a gel comprising an ionic water-soluble polymer such as a carboxyvinyl polymer as a gelling agent, a solid content of the ionic water-soluble polymer may be aggregated through interaction with an ionic component of a physiologically active substance or the like in some cases.

Besides, the present inventors have found that when a gel comprising a nonionic water-soluble polymer as a gelling agent is rubbed into the skin, crumbs are easily formed. The term "crumbs" generally means that when a composition is rubbed into the skin, a solid content contained in the composition is dried or the like to form a grime-like (pasty) lump. Besides, the present inventors have found a problem that a film formed by drying of the gel after application onto the skin (dried gel composition) is fragmented due to influence of extension and shrinkage of the skin or the like, and as a result, is easily peeled off from the skin in a scale-like shape.

Therefore, an object of the present invention is to provide a gel capable of inhibiting formation of crumbs when rubbed into the skin, and difficult to peel off in a scale-like shape even after application.

Solution to Problem

The present inventors have found that the above-described problems can be solved by a gel composition comprising a specific compound. Specifically, the present invention provides the following [1] to [6]:

[1] An emulsified gel composition, comprising a physiologically active substance, water, a gelling agent, an anti-peeling agent, and a surfactant having an HLB value of 18 to 20, in which the gelling agent is a nonionic water-soluble polymer, and the anti-peeling agent is one or more compounds selected from the group consisting of sucrose, sorbitol, polyethylene glycol, glycerin, a (meth)acrylic-based polymer compound, and a polyoxyethylene hydrogenated castor oil.

[2] The emulsified gel composition according to [1], in which the physiologically active substance comprises diclofenac or a pharmacologically acceptable salt thereof.

[3] The emulsified gel composition according to [1] or [2], in which the nonionic water-soluble polymer comprises one or more compounds selected from the group consisting of hydroxypropyl cellulose and hydrophobically-modified hydroxypropyl methyl cellulose.

[4] The emulsified gel composition according to any one of [1] to [3], in which the anti-peeling agent comprises a methyl acrylate/2-ethylhexyl acrylate copolymer.

[5] The emulsified gel composition according to any one of [1] to [4], in which the surfactant comprises at least one compound selected from the group consisting of polyoxyethylene behenyl ether, polyoxyethylene monostearyl ether, polyoxyethylene cetyl ether, and polyoxyethylene oleyl ether.

[6] The emulsified gel composition according to any one of [1] to [5], further comprising an aliphatic alcohol having 1 to 3 carbon atoms.

Advantageous Effects of Invention

An emulsified gel composition of the present invention can be used as a gel formulation, and exhibits physiological activity thereof through transdermal absorption of a physiologically active substance contained therein. Besides, according to the present invention, formation of crumbs in rubbing the emulsified gel composition into the skin can be inhibited, and even after the application, peeling in a scale-like shape is difficult to occur. Therefore, even after a volatile component is lost from the emulsified gel composition after the application, an active ingredient of the composition is easily fixed onto the skin, and is easily continuously absorbed into the skin.

Herein, the term "application feeling" means sensory evaluation comprehensively including easiness of spreading in applying a gel composition onto the skin, difficulty of the gel composition to fall down, and difficulty to form crumbs, and the term "use feeling" means sensory evaluation comprehensively including the application feeling in spreading the gel composition on the skin, the presence or absence of stickiness on the applied skin surface after spread on the skin, and occurrence or non-occurrence of peeling of a dried film.

DESCRIPTION OF EMBODIMENTS

Figure 1:
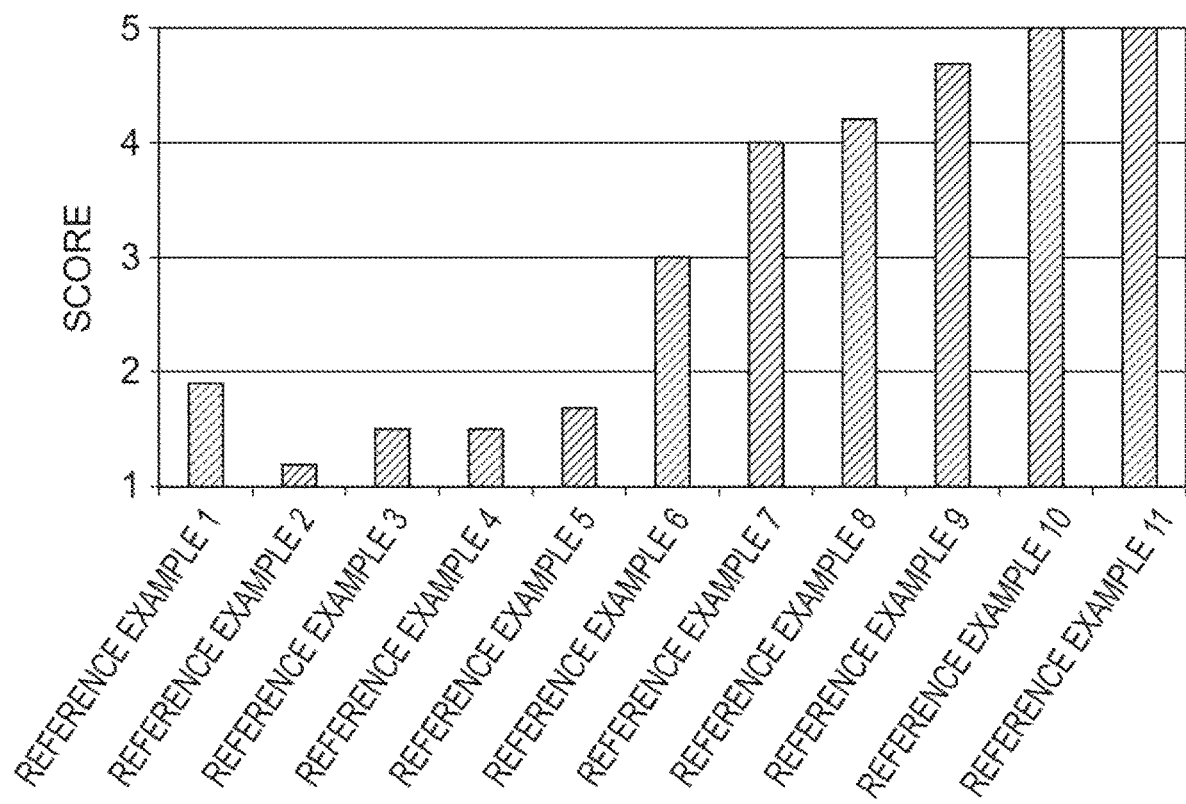
FIG. 1 is a graph illustrating results of Test 1.

The present invention will now be described in detail.

An emulsified gel composition according to one embodiment of the present embodiment comprises a physiologically active substance, water, a gelling agent, an anti-peeling agent, and a surfactant having an HLB value of 18 to 20.

Herein, the term "emulsified gel composition" means a gel composition containing an aqueous phase (dispersion medium) and an oil phase (dispersoid). The aqueous phase refers to a continuous phase containing water and a water-soluble component such as a gelling agent, and the oil phase contains a hydrophobic component or a lipophilic component, and is dispersed in the aqueous phase. The oil phase may be an oil droplet, and may be dispersed in the form of a micelle or a vesicle formed by a surfactant or the like.

The physiologically active substance is not especially limited as long as it is a substance known to have physiological activity in this industry. Examples of the physiologically active substance include antifungal agents (such as butenafine, terbinafine, naftifine, amorolfine, neticonazole, luliconazole, lanoconazole, oxiconazole, ketoconazole, miconazole, tioconazole, bifonazole, clotrimazole, econazole, itraconazole, and fluconazole), anti-inflammatory analgesics (such as indomethacin, ketoprofen, diclofenac, felbinac, flurbiprofen, loxoprofen, ibuprofen, ibuprofen piconol, guaiazulene, allantoin, piroxicam, glycyrrhizic acid, glycyrrhetinic acid, salicylic acid, methyl salicylate, and ethylene glycol monosalicylate), antihistamines (such as a mediator release inhibitor (tranilast or cromoglycic acid), histamine H1 receptor antagonists (oxatomide, mequitazine, emedastine, ebastine, loratadine, cetirizine, desloratadine, fexofenadine, astemizole, azelastine, chlorpheniramine, diphenhydramine, and ketotifen), histamine H2 receptor antagonists cimetidine, ranitidine, famotidine, and nizatidine), histamine H3 receptor antagonists (thioperamide, impromidine, mifentidine, impentamine, and clozapine), and histamine H4 receptor antagonists), essential oil components (such as 1-menthol, camphor, limonene, isopulegol, borneol, eugenol, eucalyptus oil, peppermint oil, clove oil, cinnamon oil, and tea tree oil), antiseptics (such as isopropylmethylphenol, chlorhexidine gluconate, acrinol, and benzalkonium chloride), local anesthetics (such as dibucaine, lidocaine, procaine, tetracaine, bupivacaine, propitocaine, oxybuprocaine, mepivacaine, and oxethazaine), antipruritics (such as crotamiton, ichthammol, and pine tar), blood circulation promoters (such as red pepper extract components (red pepper extract and red pepper tincture), capsaicin, dihydrocapsaicin, capsanthin, nonanoic acid vanillylamide, and nicotinic acid benzyl), steroid hormones (such as dexamethasone valerate, dexamethasone valerate acetate, dexamethasone propionate, prednisolone acetate, prednisolone valerate acetate, prednisolone, hydrocortisone butyrate propionate, hydrocortisone acetate, hydrocortisone butyrate, cortisone acetate, clobetasone butyrate, triamcinolone acetonide, diflucortolone valerate, difluprednate, diflorazone diacetate, betamethasone dipropionate, amcinonide, halcinonide, budesonide, and alclometasone dipropionate), berberine, powdered phellodendron bark, arnica tincture, and tocopherol. The physiologically active substance may be in the form of a free body of a corresponding compound, or may be in the form of a pharmacologically acceptable salt. These physiologically active substances may be used singly or in combinations of two or more. A preferable physiologically active substance is diclofenac or a pharmacologically acceptable salt thereof. Examples of the pharmacologically acceptable salt include metal salts such as sodium, potassium and calcium, and ammonium salts such as ammonia, triethylamine, diethanolamine, triethanolamine, and hydroxyethyl pyrrolidine.

The content of the physiologically active substance may be 0.001 to 15% by mass, and is preferably 0.1 to 10% by mass, and more preferably 0.5 to 7% by mass based on the mass of the whole emulsified gel composition. The physiologically active substance may be comprised in the aqueous phase or in the oil phase in the emulsified gel composition.

The water may be non-purified water, and is preferably purified water such as ion exchanged water, distilled water, or ultrafiltration water. The content of the water may be 20 to 60% by mass, and is preferably 30 to 50% by mass, and more preferably 35 to 45% by mass based on the mass of the whole emulsified gel composition. When the content of the water is 20% by mass or more, the resultant emulsified gel composition attains appropriate liquidity, and hence can be easily applied on the skin, and in addition, the applied skin surface is less sticky after the application. Besides, when the content of the water is 60% by mass or less, the gel composition applied onto the skin is more difficult to flow down.

The gelling agent may be a nonionic water-soluble polymer having thickening action, and may be a naturally derived polymer, a semi-synthetic polymer, or a synthetic polymer. Examples of the naturally derived nonionic water-soluble polymer include gum arabic, guar gum, agar, starch, locust bean gum, mannan, galactomannan, curdlan, dextran, and pullulan.

Alternatively, the gelling agent may be a semi-synthetic nonionic water-soluble polymer, and examples include semi-synthetic starch such as methyl hydroxypropyl starch and hydroxypropyl starch, semi-synthetic cellulose such as hydroxyethyl cellulose (HEC), hydroxypropyl cellulose (HPC), hydroxyethyl methyl cellulose, and hydroxypropyl methyl cellulose (HPMC), propylene glycol alginate, and a hydrophobically-modified cellulose derivative.

The hydrophobically-modified cellulose derivative refers to a derivative of cellulose obtained by introducing a hydrophobic group into a hydroxy group of cellulose or semi-synthetic cellulose. The hydrophobic group may be an alkyl group or an alkenyl group having 4 to 30 carbon atoms, and may be an alkyl group or an alkenyl group having 12 to 24 carbon atoms such as a cetyl group, a lauryl group, a stearyl group, or an oleyl group. Besides, the hydrophobic group may arbitrarily have an ether bond or a hydroxy group. Examples of the hydrophobically-modified cellulose derivative include hydrophobically-modified hydroxypropyl methyl cellulose (hydrophobically-modified HPMC), and hydrophobically-modified hydroxyethyl cellulose (hydrophobically-modified HEC). Specifically, the "hydrophobically-modified HPMC" refers to HPMC into which a small amount of hydrophobic group has been introduced. The hydrophobically-modified cellulose derivative is more excellent in thickening effect than a cellulose derivative such as HEC or HPC, and excellent also in compatibility with alcohol. The hydrophobically-modified cellulose derivative easily forms a thixotropic gel, is more excellent in shape retention, and can further inhibit stickiness otherwise caused after the application.

The hydrophobically-modified HPMC may comprise 0 to 33% by mass of a methoxy group, preferably comprises 10 to 30% by mass of a methoxy group, more preferably comprises 21.5 to 30% by mass of a methoxy group, and further preferably comprises 21.5 to 24% by mass or 27 to 30% by mass of a methoxy group based on the mass thereof. The hydrophobically-modified HPMC may contain 0 to 20% by mass of a hydroxypropyloxy group, preferably comprises 4 to 15% by mass of a hydroxypropyloxy group, and more preferably comprises 7 to 11% by mass of a hydroxypropyloxy group based on the mass thereof. The hydrophobically-modified HPMC may be HPMC having a stearyloxy group (stearyloxy HPMC). The stearyloxy HPMC may comprise 0.3 to 4.5% by mass of a stearyloxy hydroxypropyloxy group, preferably comprises 0.3 to 2% by mass of a stearyloxy hydroxypropyloxy group, and more preferably comprises 0.3 to 0.6% by mass or 1 to 2% by mass of a stearyloxy hydroxypropyloxy group based on the mass thereof. As the hydrophobically-modified HPMC, for example, SANGELOSE 60L, 60M, 90L, and 90M (all trade names, manufactured by Daido Chemical Corporation) may be used.

Alternatively, the gelling agent may be a synthesized nonionic water-soluble polymer, and examples include polyvinyl alcohol, polyvinyl methyl ether, polyvinyl pyrrolidone, and polyacrylamide.

The gelling agent preferably comprises one or more compounds selected from the group consisting of HPMC, HPC, and hydrophobically-modified HPMC, and more preferably comprises one or more compounds selected from the group consisting of HPC and hydrophobically-modified HPMC. When HPC or hydrophobically-modified HPMC is comprised, the viscosity of the resultant gel composition can be easily improved, so as to more easily inhibit the gel composition from falling off from the skin. Besides, spreadability in applying the gel composition onto the skin is further improved, and stickiness otherwise caused on the applied skin surface after rubbing the gel composition can be further inhibited.

A content of the gelling agent may be 0.5 to 5% by mass, is preferably 0.8 to 4% by mass, and more preferably 1.1 to 3% by mass based on the mass of the whole emulsified gel composition.

It is most preferable that the emulsified gel composition of the present embodiment does not comprise an ionic polymer. The emulsified gel composition may comprise, however, an ionic polymer such as a carboxyvinyl polymer, carboxymethyl cellulose, polyacrylic acid and a salt of any of these as long as the effects of the present invention are not impaired. When the emulsified gel composition comprises an ionic polymer, a content of the ionic polymer is preferably 1% by mass or less, and more preferably 0.5% by mass or less based on the mass of the whole emulsified gel composition. When the emulsified gel composition comprises a carboxyvinyl polymer, interaction with a specific physiologically active substance such as diclofenac sodium is caused, and hence, the ionic polymer is easily aggregated, and in addition, crumbs are easily formed in rubbing the emulsified gel composition onto the skin. As the content of the ionic polymer decreases, the resultant emulsified gel composition exhibits better effects. When the emulsified gel composition comprises HPC or hydrophobically-modified HPMC, the aggregation as described above is not caused, the viscosity can be appropriately increased, and in the application onto the skin, falling down and crumbs formation of the gel composition can be inhibited. In addition, the emulsified gel composition comprising hydrophobically-modified HPMC is excellent in the spreadability in the application, and tends to be less sticky on the applied skin surface after the application.

The anti-peeling agent of the present embodiment is a component capable of inhibiting generation of a peeled substance in a scale-like shape found by the present inventors. When the emulsified gel composition comprises the anti-peeling agent, even after a volatile component is lost following the application of the gel composition, the physiologically active substance in the gel composition can be easily retained on the skin.

The anti-peeling agent is specifically one or more compounds selected from the group consisting of sucrose, sorbitol, polyethylene glycol, glycerin, a (meth)acrylic-based polymer compound, and a polyoxyethylene hydrogenated castor oil.

The polyethylene glycol is not limited as long as it is polyethylene glycol usually acceptable in the field of pharmaceuticals. The polyethylene glycol preferably has an average molecular weight of 200 to 600, more preferably has an average molecular weight of 300 to 500, and further preferably has an average molecular weight of 380 to 420. A specific example of the polyethylene glycol includes macrogol 400.

The glycerin may be glycerin usually used in the field of pharmaceuticals.

The (meth)acrylic-based polymer compound is a polymer comprising a (meth)acrylic acid alkyl ester as a monomer, and has adhesiveness to human skin at ordinary temperature. Herein, the term "(meth)acrylic acid" means one of or both of acrylic acid and methacrylic acid, and similar terms have similar meanings.

The (meth)acrylic-based polymer compound may be a polymer constituted by a single (meth)acrylic acid alkyl ester, or may be a copolymer constituted by a plurality of (meth)acrylic acid alkyl esters. Alternatively, the (meth)acrylic-based polymer compound may be a copolymer of a (meth)acrylic acid alkyl ester and a second monomer.

An alkyl group in the (meth)acrylic acid alkyl ester is preferably an alkyl group having 2 to 9 carbon atoms. Alternatively, an alkyl group in the (meth)acrylic acid alkyl ester is preferably an alkyl group having 8 to 12 carbon atoms. The (meth)acrylic-based polymer compound preferably comprises, as a principal monomer, such a (meth) acrylic acid alkyl ester. When such a (meth)acrylic-based polymer compound is comprised, a glass transition temperature is lowered, and appropriate adhesiveness to the skin can be imparted.

The glass transition temperature of the (meth)acrylic-based polymer compound is preferably $-20°$ C. or less, and more preferably $-40°$ C. or less. In addition, the glass transition temperature of the (meth)acrylic-based polymer compound is preferably $-120°$ C. or more, and more preferably $-100°$ C. or more.

The second monomer may be a monomer excluding the (meth)acrylic acid alkyl ester, and examples include a monomer having a polymerizable unsaturated bond such as a monomer having a hydroxy group such as 2-hydroxyethyl (meth)acrylate, or hydroxypropyl (meth)acrylate; a monomer having a carboxy group such as (meth)acrylic acid, itaconic acid, crotonic acid, or maleic acid; a carboxylic acid derivative monomer such as maleic anhydride, or maleic acid ester; a monomer having an amide group such as N,N-dimethyl acrylamide, or N-butyl (meth)acrylamide; vinyl pyrrolidone; vinyl alcohol; acrylonitrile; vinyl acetate; and styrene.

Preferable examples of the (meth)acrylic acid alkyl ester include ethyl (meth)acrylate, n-butyl (meth)acrylate, octyl (meth)acrylate, 2-ethylhexyl (meth)acrylate, hydroxyethyl (meth)acrylate, dodecyl (meth)acrylate, and methyl (meth) acrylate. Preferable examples of the second monomer include vinyl acetate, vinyl pyrrolidone, and (meth)acrylic acid.

Examples of the (meth)acrylic-based polymer compound include a methyl acrylate/2-ethylhexyl acrylate copolymer, and a methacrylic acid/n-butyl acrylate copolymer.

The methyl acrylate/2-ethylhexyl acrylate copolymer may be prepared by copolymerizing methyl acrylate and 2-ethylhexyl acrylate, or a commercially available copolymer may be used. An example of the commercially available copolymer includes Nikasol TS620 (manufactured by NIPPON CARBIDE INDUSTRIES CO., INC.). From the viewpoint of easiness of mixing with another component, the methyl acrylate/2-ethylhexyl acrylate copolymer may be used in the form of an aqueous emulsion. A specific example includes an aqueous emulsion of Nikasol TS620 (trade name, manufactured by NIPPON CARBIDE INDUSTRIES CO., INC.) or the like. Nikasol TS620 is an aqueous emulsion of a methyl acrylate/2-ethylhexyl acrylate copolymer resin, and comprises POE nonyl phenyl ether (HLB value=17.1). Besides, according to Japanese Pharmaceutical Excipients (2013), when Nikasol TS620 is evaporated to dryness on a water bath and dried at 105° C. for 3 hours, the resultant evaporation residue has a mass of 57 to 61%. The term "POE" means "polyoxyethylene". When the anti-peeling agent is an aqueous emulsion of the (meth)acrylic-based polymer compound (such as a methyl acrylate/2-ethylexyl acrylate copolymer), the emulsion state can be changed through mixture with another component comprised in the emulsified gel composition. For example, in the emulsified gel composition, a methyl acrylate/2-ethylhexyl acrylate copolymer and a POE nonyl phenyl ether form a part of the oil phase, and water corresponding to the dispersion medium of the emulsion can be distributed to the aqueous phase.

The methacrylic acid/n-butyl acrylate copolymer may be prepared by copolymerizing methacrylic acid and n-butyl acrylate, or a commercially available copolymer may be used. Examples of the commercially available copolymer include PRIMAL N58ONF (trade name, manufactured by Nippon Acrylic Chemical Co., Ltd.), and Ultrasol W50 (trade name, manufactured by Aica Kogyo Co., Ltd.). From the viewpoint of easiness of mixing with another component, the methacrylic acid/n-butyl acrylate copolymer may be used in the form of an aqueous emulsion.

The polyoxyethylene hydrogenated castor oil used as the anti-peeling agent has an HLB value less than 18. The polyoxyethylene hydrogenated castor oil has the number of polyoxyethylene moles added of preferably 10 to 100, more preferably 40 to 80, and particularly preferably 60. For example, POE (10) hydrogenated castor oil (trade name: NIKKOL HCO-10) has an HLB value of 6.5, and POE (100) hydrogenated castor oil (trade name: NIKKOL HCO-100) has an HLB value of 16.5. The number of polyoxyethylene moles added refers to an average number of moles of an ethylene oxide unit added. A numerical value in parentheses following the "POE" means the number of polyoxyethylene moles added.

The content of the anti-peeling agent may be 1 to 10% by mass, is preferably 2 to 8% by mass, and more preferably 3 to 7% by mass based on the mass of the whole emulsified gel composition. When the (meth)acrylic-based polymer compound is in the form of an aqueous emulsion, the mass of the whole emulsion preferably falls in the above-described range. When the content of the anti-peeling agent is 1% by mass or more, flexibility, toughness, softness or adhesiveness is imparted to the film (dried emulsified gel composition), and the generation of a peeled substance in a scale-like shape can be further inhibited. When the content of the anti-peeling agent is 10% by mass or less, there is a tendency that the application feeling of the gel composition is minimally impaired.

The surfactant is not especially limited as long as it is a nonionic surfactant having an HLB value of 18 to 20. An HLB value refers to a numerical value corresponding to hydrophilic-lipophilic balance of a surfactant, and is defined in a range of 0 to 20. An HLB value closer to 0 (zero) means stronger lipophilicity, and an HLB value closer to 20 means stronger hydrophilicity. For example, polyethylene glycol monolaurate (10E.O.) (trade name: NIKKOL MYL-10) has an HLB value of 12.5, and POE (15) cetyl ether (trade name: NIKKOL BC-15) has an HLB value of 15.5. When a surfactant having an HLB value of 18 to 20 is comprised, the formation of crumbs can be further inhibited in applying the gel composition onto the skin.

Examples of such a surfactant include polyoxyethylene alkyl ethers such as POE (23) cetyl ether, POE (25) cetyl ether, POE (30) cetyl ether, POE (40) cetyl ether, POE (20) stearyl ether, and POE (30) behenyl ether, polyoxyethylene alkenyl ethers such as POE (50) oleyl ether, polyoxyethylene lauryl ether, POE (21) lauryl ether, and POE (25) lauryl ether, polyoxyethylene fatty acid esters such as polyethylene glycol monostearate (45E.O.), polyethylene glycol monostearate (55E.O.), and POE monostearate, and polyoxyethylene phytosterol. More specifically, any one of NIKKOL BC-23, NIKKOL BC-25, NIKKOL BC-30, NIKKOL BC-40, NIKKOL BS-20, NIKKOL BO-50V, NIKKOL BB-30, NIKKOL MYS-45V, NIKKOL MYS-45MV, NIKKOL MYS-55V, NIKKOL MYS-55MV, NIKKOL BL-21, NIKKOL BL-25, and NIKKOL BPS-30 (all trade names, manufactured by Nikko Chemicals Co., Ltd.) may be used as the surfactant. In the above description, a numerical value described in parentheses following POE refers to an average number of moles of an oxyethylene unit added.

When the surfactant has a polyoxyethylene group, the HLB value can be changed in accordance with the number of polyoxyethylene moles added. For example, an average number of moles of an oxyethylene unit added in the polyoxyethylene alkyl ether or the polyoxyethylene alkenyl ether may be 20 to 60, or may be 20 to 55.

Besides, an alkyl group of the polyoxyethylene alkyl ether or an alkenyl group of the polyoxyethylene alkenyl ether is preferably an alkyl group or an alkenyl group having 10 to 24 carbon atoms, more preferably has 16 to 24 carbon atoms, and further preferably has 18 to 22 carbon atoms. A preferable surfactant is POE behenyl ether, POE stearyl ether, POE oleyl ether, POE lauryl ether or POE cetyl ether. POE behenyl ether more preferably has an average number of moles of an oxyethylene unit added of 30 to 60. POE stearyl ether, POE oleyl ether or POE lauryl ether more preferably has an average number of moles of an oxyethylene unit added of 30 to 60. POE cetyl ether more preferably has an average number of molecules of an oxyethylene unit added of 23 to 60.

Measurement of an HLB value may be performed by a method known to those skilled in the art. The measurement of an HLB value is performed by, for example, a method in which a surfactant having a known HLB used as a standard and a sample having an unknown HLB are respectively used to emulsify an oil used as a standard (such as liquid paraffin) and purified water, and a combination ratio at which the most stable emulsion can be obtained is compared between the standard and the sample. A composition used in the measurement may have a composition containing 40% by mass of an oil phase, 56% by mass of purified water, and 4% by mass of a surfactant or a sample having an unknown HLB. Besides, the measurement method may be determined by referring to description of JP 2010-099017 A, JP 2005-272750 A, JP 2002-301352 A and the like.

The content of the surfactant may be 0.5 to 4% by mass, is preferably 1 to 3% by mass, and more preferably 1.5 to 2.5% by mass based on the mass of the whole emulsified gel composition. When the content of the surfactant is 0.5% by mass or more, there is a tendency that the formation of crumbs can be further inhibited. When the content of the surfactant is 4% by mass or less, the application feeling onto the skin of the gel composition is more excellent, and the applied skin surface tends to be less sticky.

The emulsified gel composition of the present embodiment may further comprise a lower alcohol. The lower alcohol functions as a liquid medium forming a gel together with the water-soluble polymer in the gel base. Besides, when the lower alcohol is comprised, a drying time after the application of the composition can be shortened, and the use feeling is further improved. The lower alcohol may be an aliphatic alcohol having 1 to 6 carbon atoms, and is preferably an aliphatic alcohol having 1 to 3 carbon atoms. As the alcohol has a larger number of carbon atoms, the drying takes longer time after the application. Examples of the lower alcohol include ethanol and isopropanol, and ethanol is preferred. These lower alcohols may be used singly or in combinations of two or more.

The content of the lower alcohol is not especially limited, and may be, based on the mass of the water comprised in the emulsified gel composition, 0.5 to 2-fold amount, is preferably 0.6 to 1.5-fold amount, and more preferably 0.8 to 1.2-fold amount. When the content of the lower alcohol is 0.5-fold or larger amount of the content of the water, the application feeling can be further improved, and the drying time after the application can be further shortened. When the content of the lower alcohol is 2-fold or smaller amount of the content of the water, swelling or dissolution of the gelling agent can be further accelerated, there is a tendency that the emulsified state of the gel composition can be easily retained, and stimulus to the skin by the lower alcohol can be further reduced.

When the emulsified gel composition of the present embodiment comprises the hydrophobically-modified cellulose derivative as the gelling agent, and/or comprises the (meth)acrylic-based polymer compound (such as a methyl acrylate/2-ethylhexyl acrylate copolymer) as the anti-peeling agent, deterioration of storage stability of the gel composition can be further inhibited even through the content of the lower alcohol in the gel composition is 0.5 to 2-fold amount of the water.

The emulsified gel composition of the present embodiment may further comprise an optional component such as an oily component, an absorption enhancer, a dissolving agent, a stabilizer, a pH regulator, a preservative, or an anti-rash agent.

The emulsified gel composition of the present embodiment is a gel in which a water-insoluble component such as an oily component forms an oil phase in an aqueous phase containing a water-soluble component. The emulsified gel composition of the present embodiment has appropriate viscosity, is difficult to fall off from the skin when applied onto the skin, and is excellent also in the use feeling.

The oily component may be a component capable of constituting the oil phase of the emulsified gel composition. Examples of the oily component include vegetable oils such as avocado oil, linseed oil, olive oil, orange oil, chamomile oil, sesame oil, wheat germ oil, rice bran oil, safflower oil, squalane (phytosqualane, olive squalane or the like), squalene, soybean oil, tea oil, evening primrose oil, camellia oil, turpentine oil, corn oil, rapeseed oil, palm oil, peppermint oil, castor oil, sunflower oil, jojoba oil, cottonseed oil, coconut oil, eucalyptus oil, peanut oil, lemon oil, and rose oil, animal fats and oils such as beef tallow, squalane, squalene, turtle oil, butterfat, horse oil, mink oil, lanolin, and egg yolk oil, cholesterols (such as cholesterol and phytosterol), fatty acids (such as capric acid and oleic acid), aliphatic alcohols (such as oleyl alcohol, lauryl alcohol, and isostearyl alcohol), fatty acid esters (such as diisopropyl adipate and isopropyl palmitate), paraffin oil, and silicone oil.

The absorption enhancer may be any one having a function to enhance transdermal absorption of the physiologically active substance. Examples of the absorption enhancer include fatty acid esters such as propylene carbonate, diethyl sebacate, and diisopropyl adipate, crotamiton, and propylene glycol.

The dissolving agent may be any one used in this industry and capable of dissolving a component of the gel composition of the present embodiment. Examples of the dissolving agent include higher alcohols (such as cetyl alcohol, stearyl alcohol, behenyl alcohol, oleyl alcohol, and octyldodecanol), fatty acid esters (such as isopropyl myristate, octyldodecyl myristate, cetyl myristate, myristyl myristate, diethyl sebacate, diisopropyl sebacate, diisopropyl adipate, oleyl oleate, hexyl laurate, cetyl isooctanoate, medium-chain triglyceride, and propylene glycol fatty acid ester), N-methyl-2-pyrrolidone, triacetin, benzyl alcohol, 1-menthyl glyceryl ether, polyhydric alcohols (such as glycerin, propylene glycol, polyethylene glycol, polypropylene glycol, sorbitol, 1,3-butylene glycol, dipropylene glycol, batyl alcohol (glycerin-α-monostearyl ether)), and dimethyl sulfoxide.

The stabilizer may be any component capable of inhibiting decomposition of the physiologically active substance by UV or oxygen. Examples of the stabilizer include ascorbic acid, ascorbyl palmitate, propyl gallate, dibutyl hydroxytoluene, dibutyl hydroxyanisole, tocopherol, tocopherol acetate, sodium sulfite, sodium hydrogen sulfite, sodium pyrosulfite, 2-mercaptobenzimidazole, and oxybenzone.

The pH regulator is a component to be added for making the pH of the emulsified gel composition suitable to the application onto the skin. Besides, the pH of the emulsified gel composition is preferably a pH suitable for the storage stability and the transdermal absorption of the physiologically active substance. Examples of the pH regulator include an acidifying agent such as citric acid, acetic acid, lactic acid, or phosphoric acid, and an alkalizing agent such as monoethanolamine, diethanolamine, or triethanolamine.

For obtaining the emulsified gel composition of the present embodiment, for example, the respective components can be weighed, and mixed by stirring or the like to obtain an emulsified composition.

In preparation of the gel composition, a hydrophobic component may be added and mixed after forming the aqueous phase by mixing a water-soluble component, or a water-soluble component may be added and mixed after forming the oil phase by mixing a hydrophobic component, or another method may be employed.

As a method for emulsifying the gel composition, the components may be simply mixed, or high shear force may be applied in mixing by using a high pressure homogenizer or a high-speed stirrer. Besides, the composition may be emulsified under heating or cooling. The emulsification method may be appropriately selected by those skilled in the art in consideration of a combination of a water-soluble component and a hydrophobic component, and the presence/absence of an emulsifier.

EXAMPLES

Test 1: Evaluation of Peeling in Scale-like Shape

When a gel composition is applied onto a forearm of a subject, the gel composition is gradually dried to form a film. Thereafter, due to the influence of expansion and shrinkage of the skin or the like, the film is gradually peeled in a scale-like shape, and the whole film is peeled off from the skin ultimately. Therefore, it is significant, as evaluation of close adhesiveness of a gel composition onto the skin, to evaluate the number of film pieces in a scale-like shape about to peel off from the skin.

Respective components were mixed as shown in Tables 1 to 3 to prepare gel compositions of Reference Examples 1 to 11. Each numerical value shown in Tables 1 and 2 is in "% by mass", and each compound shown in Table 3 was used as a component A. Stearyloxy HPMC (stearyloxy hydroxypropyloxy group=0.3 to 0.6% by mass) was used as hydrophobically-modified HPMC, and Nikasol TS620 (trade name, manufactured by NIPPON CARBIDE INDUSTRIES CO., INC.) was used as a methyl acrylate/2-ethylhexyl acrylate copolymer. The term "Balance" shown in Tables 1 and 2 means that purified water and ethanol in a mass ratio of 1:1 were added to make the mass of the whole composition 100. Additional Components shown in Tables 1 and 2 refer to a physiologically active substance excluding diclofenac sodium, and another optional component.

TABLE 1

| | Reference Example 1 | Reference Example 2 | Reference Example 3 | Reference Example 4 | Reference Example 5 |
|---|---|---|---|---|---|
| Diclofenac Sodium | 1 | 1 | 1 | 1 | 1 |
| Hydrophobically-modified HPMC | 0.9 | 0.9 | 0.9 | 0.9 | 0.9 |
| HPC | 1 | 1 | 1 | 1 | 1 |
| Ethylcellulose | — | 0.2 | — | — | — |
| Castor Oil | — | — | 1 | — | — |
| Sucrose Fatty Acid Ester | — | — | — | 3.5 | — |
| Surfactant | 0 | 0 | 0 | 0 | 0 |
| Propylene Glycol | 5 | 5 | 5 | 5 | 10 |
| Diisopropyl Adipate | 7 | 7 | 7 | 7 | 7 |
| Purified Water | Balance | Balance | Balance | Balance | Balance |
| Ethanol | Balance | Balance | Balance | Balance | Balance |
| Additional Components | 4.83 | 4.83 | 4.83 | 4.83 | 4.83 |
| Total | 100 | 100 | 100 | 100 | 100 |

TABLE 2

| | Content |
|---|---|
| Diclofenac Sodium | 1 |
| Hydrophobically-modified HPMC | 0.9 |
| HPC | 1 |
| Component A | 5 |
| Surfactant | 0 |
| Propylene Glycol | 5 |
| Diisopropyl Adipate | 7 |
| Purified Water | Balance |
| Ethanol | Balance |
| Additional Components | 4.83 |
| Total | 100 |

TABLE 3

| | Component A |
|---|---|
| Reference Example 6 | Sucrose |
| Reference Example 7 | Sorbitol |
| Reference Example 8 | Polyethylene Glycol 400 |
| Reference Example 9 | Glycerin |
| Reference Example 10 | Nikasol TS-620 |
| Reference Example 11 | POE Hydrogenated Castor Oil 60 |

Each of the thus obtained gel compositions was applied, in an amount of 0.5 g, onto the skin of a forearm of 5 subjects (healthy adults) in an application area of 50 cm$^2$, and about 3 hours later, a peeling state of a film (dried gel composition) was visually observed. The results of the observation were scored in accordance with the criteria shown in Table 4, and an average thereof was calculated.

TABLE 4

| Score | Observation Result |
|---|---|
| 1 | Peeling was observed in a considerably large amount. (An area having scale-like shaped substances corresponded to more than 30% and 100% or less of the application area.) |
| 2 | Peeling was observed in a rather large amount. (An area having scale-like shaped substances corresponded to more than 10% and 30% or less of the application area.) |
| 3 | Peeling was observed in a small amount. (An area having scale-like shaped substances corresponded to more than 5% and 10% or less of the application area.) |
| 4 | Peeling was observed in a slight amount. (An area having scale-like shaped substances corresponded to more than 0% and 5% or less of the application area.) |
| 5 | Peeling was not observed. |

An average of the obtained scores was calculated, and the results are shown in Table 5 and FIG. 1. The gel compositions of Reference Examples 2 to 5 had lower scores as compared with the gel composition of Reference Example 1 as a control. Specifically, this result means that the gel compositions of Reference Examples 2 to 5 rather increased in the peeling of the films in a scale-like shape. On the other hand, the gel compositions of Reference Examples 6 to 11 had higher scores as compared with the gel composition of Reference Example 1, and thus, the peeling in a scale-like shape was inhibited.

TABLE 5

|  | Average Score |
| --- | --- |
| Reference Example 1 | 1.9 |
| Reference Example 2 | 1.2 |
| Reference Example 3 | 1.5 |
| Reference Example 4 | 1.5 |
| Reference Example 5 | 1.7 |
| Reference Example 6 | 3 |
| Reference Example 7 | 4 |
| Reference Example 8 | 4.2 |
| Reference Example 9 | 4.7 |
| Reference Example 10 | 5 |
| Reference Example 11 | 5 |

Test 2: Evaluation of Crumbs

Respective components were mixed as shown in Tables 6 and 7 to prepare gel compositions. Each numerical value shown in Table 6 is in "% by mass", and each component shown in Table 7 was used as a component B. The used hydrophobically-modified HPMC was the same as that described in Test 1. The term "Balance" shown in Table 6 means that purified water and ethanol in a mass ratio of 1:1 were added to make the mass of the whole composition 100. Additional Components shown in Table 6 refer to a physiologically active substance excluding diclofenac sodium, and another optional component.

TABLE 6

|  | Content |
| --- | --- |
| Diclofenac Sodium | 1 |
| Hydrophobically-modified HPMC | 0.9 |
| HPC | 1 |
| Nikasol TS-620 | 5 |
| Component B | 1 |
| 1-Menthyl Glyceryl Ether | 2.5 |
| Propylene Glycol | 5 |
| Diisopropyl Adipate | 7 |
| Purified Water | Balance |
| Ethanol | Balance |
| Additional Components | 5.01 |
| Total | 100 |

TABLE 7

|  | Component B | HLB Value |
| --- | --- | --- |
| Comp. Example 1 | Mixed Solvent of Water and Ethanol (mass ratio = 1:1) | — |
| Comp. Example 2 | Polysorbate 20 | 16.9 |
| Comp. Example 3 | POE (10) Sodium Lauryl Ether Phosphate | 17.0 |

TABLE 7-continued

|  | Component B | HLB Value |
| --- | --- | --- |
| Example 1 | POE (30) Behenyl Ether | 18.0 |
| Example 2 | POE (45) Monostearate | 18.0 |
| Example 3 | POE (40) Cetyl Ether | 20.0 |

Each of the thus obtained gel compositions was rubbed, in an amount of 0.5 g, onto the skin of a forearm of 5 subjects (healthy adults) to be spread in an application area of 50 cm$^2$ for 10 to 30 seconds, and thereafter, the dried composition was observed with a touch with a finger or visually to evaluate the extent of crumbs. Evaluation results were scored in accordance with the following criteria, and an average thereof was calculated.
<Evaluation Criteria>
100: No crumbs were formed.
75: Crumbs were slightly formed.
50: Crumbs were formed (in a small amount).
25: Crumbs were formed (in a large amount).
0: Crumbs were formed (in a considerable amount).

Figure 2:
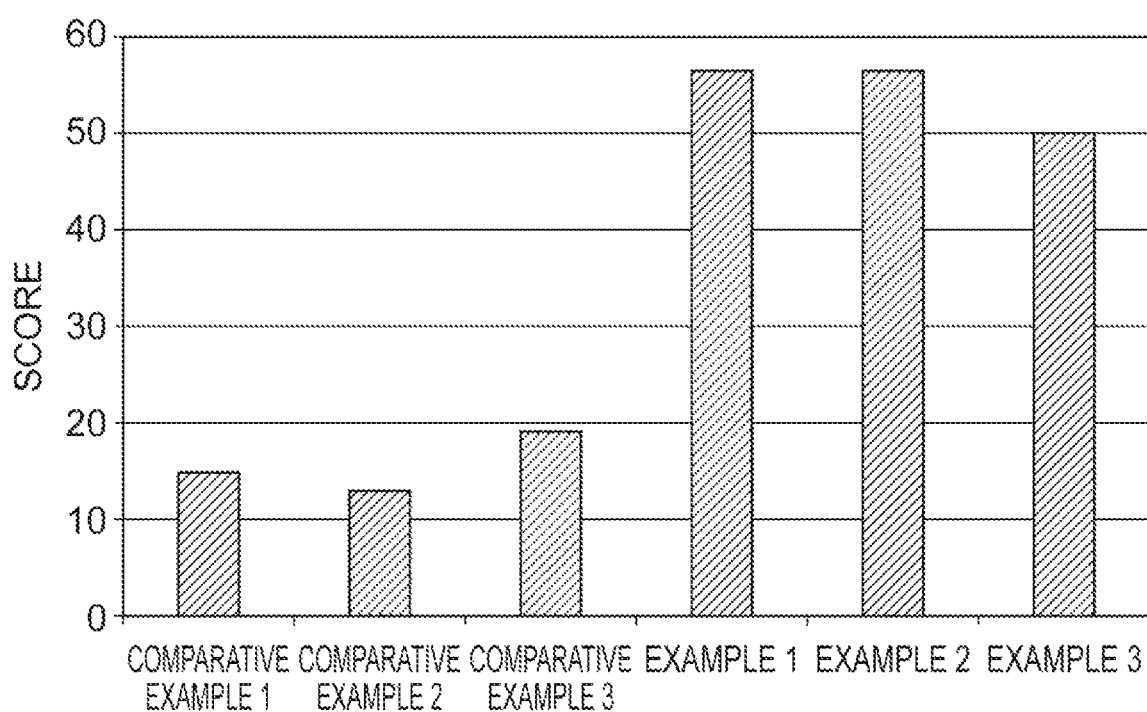
FIG. 2 is a graph illustrating results of Test 2.

An average of the obtained scores was calculated, and shown in Table 8 and FIG. 2. The gel compositions of Examples 1 to 3 could remarkably inhibit the formation of crumbs as compared with the gel compositions of Comparative Examples 1 to 3.

TABLE 8

|  | Average Score |
| --- | --- |
| Comp. Example 1 | 15 |
| Comp. Example 2 | 13 |
| Comp. Example 3 | 19 |
| Example 1 | 56 |
| Example 2 | 56 |
| Example 3 | 50 |

Test 3: Evaluation of Storage Stability of Gel Composition

Respective components were mixed as shown in Tables 9 and 10 to prepare gel compositions of Reference Examples 12 to 24. Each numerical value shown in Table 9 is in "% by mass", and each component shown in Table 10 was used as a component C. The used hydrophobicaly-modified HPMC was the same as that described in Test 1. The term "Balance" shown in Table 9 means that purified water and ethanol in a mass ratio of 1:1 were added to make the mass of the whole composition 100. Additional Components shown in Table 9 refer to a physiologically active substance excluding diclofenac sodium, and another optional component.

TABLE 9

|  | Content |
| --- | --- |
| Diclofenac Sodium | 1 |
| Hydrophobically-modified HPMC | 0.9 |
| HPC | 1 |
| Component C | 3 |
| Dibutyl Hydroxytoluene | 0.1 |
| 1-Menthyl Glyceryl Ether | 2.5 |
| Propylene Glycol | 5 |
| Diisopropyl Adipate | 7 |
| Purified Water | Balance |
| Ethanol | Balance |
| Additional Components | 4.97 |
| Total | 100 |

TABLE 10

|  | Component C | HLB Value |
|---|---|---|
| Reference Example 12 | None | — |
| Reference Example 13 | Glyceryl Monostearate | 4.0 |
| Reference Example 14 | Propylene Glycol Monostearate | 3.5 |
| Reference Example 15 | Decaglyceryl Pentaoleate | 3.5 |
| Reference Example 16 | Ethylene Glycol Monostearate | 3.5 |
| Reference Example 17 | Sorbitan Sesquioleate | 4.0 |
| Reference Example 18 | Sorbitan Monoisostearate | 5.0 |
| Reference Example 19 | POE (6) Sorbit Beeswax | 7.5 |
| Reference Example 20 | POE (5) Glyceryl Oleate | 9.5 |
| Reference Example 21 | POE (20) Sorbitan Trioleate | 11.0 |
| Reference Example 22 | Polyethylene Glycol Monostearate (45EO) | 18.0 |
| Reference Example 23 | Polyoxyethylene Phytosterol | 18.0 |
| Reference Example 24 | POE (40) Cetyl Ether | 20.0 |

Each of the thus obtained gel compositions was enclosed in a test tube in a depth of the composition of 10 cm, and the resultant test tube was allowed to stand in a thermostat chamber at 60° C. After 13 days passed, the test tube was taken out of the thermostatic chamber, and the gel composition contained therein was visually observed through a side surface of the test tube to measure a thickness of a layer (oil layer) separated as an upper layer.

Figure 3:
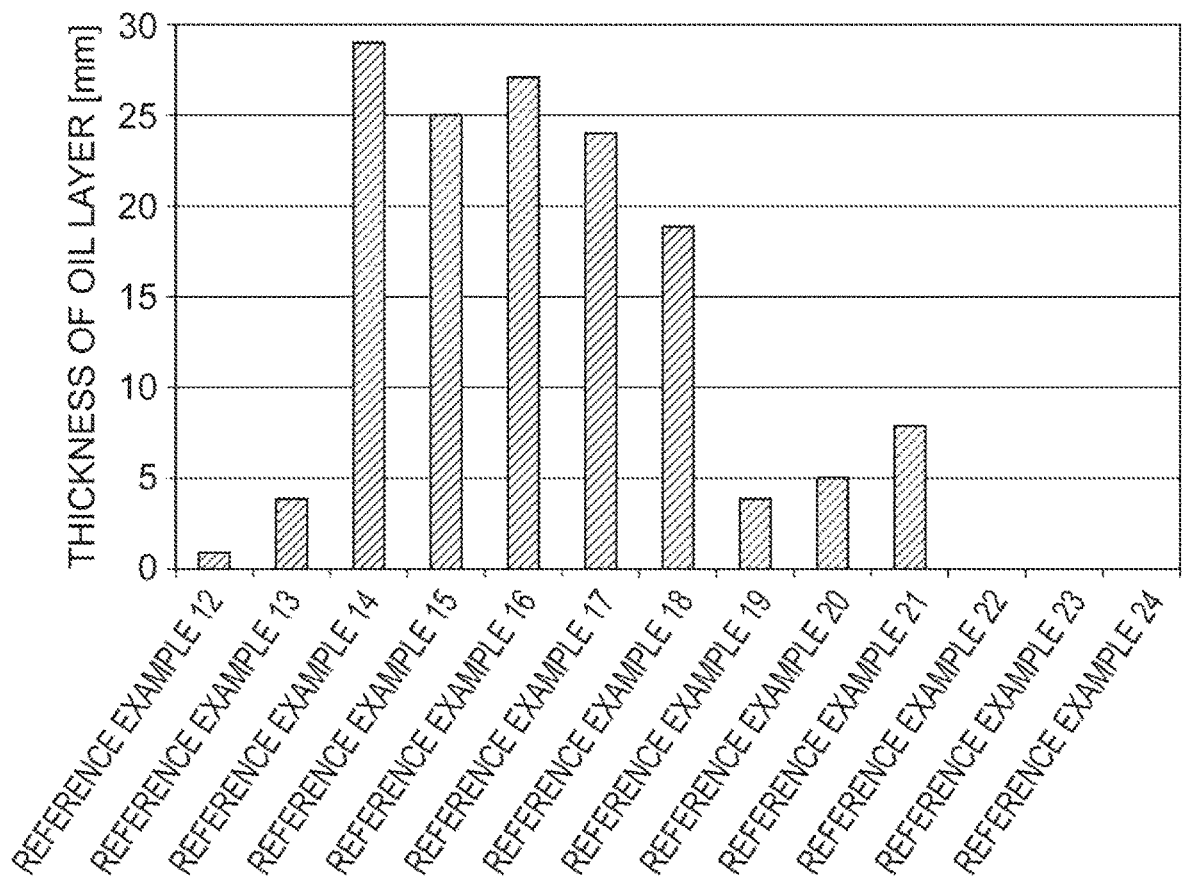
FIG. 3 is a graph illustrating results of Test 3.

The results are shown in Table 11 and FIG. 3. In the gel compositions of Reference Examples 13 to 21, the amount of the oil layer separated during the storage at 60° C. for 13 days was larger as compared with that in the gel composition of Reference Examples 12 not comprising a surfactant, and thus, it was found that the storage stability of these gel compositions was lowered. On the other hand, in the gel compositions of Reference Examples 22 to 24, the oil layer was not separated after the storage, and a homogeneous state was retained.

TABLE 11

|  | Thickness of Oil Layer [mm] |
|---|---|
| Reference Example 12 | 1 |
| Reference Example 13 | 4 |
| Reference Example 14 | 29 |
| Reference Example 15 | 25 |
| Reference Example 16 | 27 |
| Reference Example 17 | 24 |
| Reference Example 18 | 19 |
| Reference Example 19 | 4 |
| Reference Example 20 | 5 |
| Reference Example 21 | 8 |
| Reference Example 22 | 0 |
| Reference Example 23 | 0 |
| Reference Example 24 | 0 |

Test 4: Evaluation of Peeling in Scale-like Shape

Respective components were mixed as shown in Tables 12 and 13 to prepare gel compositions of Examples 4 to 9 and Comparative Examples 4 to 8. Each numerical value shown in Tables 12 and 13 is in "% by mass". Used hydrophobically-modified HPMC was the same as that described in Test 1, and Nikasol TS620 (trade name, manufactured by NIPPON CARBIDE INDUSTRIES CO., INC.) was used as a methyl acrylate/2-ethylhexyl acrylate copolymer. The term "Balance" shown in Tables 12 and 13 means that purified water and ethanol in a mass ratio of 1:1 were added to make the mass of the whole composition 100. Additional Components shown in Tables 12 and 13 refer to a physiologically active substance excluding diclofenac sodium, and another optional component. POE (30) Behenyl Ether is a surfactant having an HLB of 18.0.

TABLE 12

|  | Comp. Example 4 | Comp. Example 5 | Comp. Example 6 | Comp. Example 7 | Comp. Example 8 |
|---|---|---|---|---|---|
| Diclofenac Sodium | 1 | 1 | 1 | 1 | 1 |
| Hydrophobically-modified HPMC | 0.9 | 0.9 | 0.9 | 0.9 | 0.9 |
| HPC | 1 | 1 | 1 | 1 | 1 |
| Ethylcellulose | — | 0.2 | — | — | — |
| Castor Oil | — | — | 1 | — | — |
| Sucrose Fatty Acid Ester | — | — | — | 3.5 | — |
| Propylene Glycol | 5 | 5 | 5 | 5 | 10 |
| Diisopropyl Adipate | 7 | 7 | 7 | 7 | 7 |
| POE (30) Behenyl Ether | 0.5 | 0.5 | 0.5 | 0.5 | 0.5 |
| Purified Water | Balance | Balance | Balance | Balance | Balance |
| Ethanol | Balance | Balance | Balance | Balance | Balance |
| Additional Components | 4.83 | 4.83 | 4.83 | 4.83 | 4.83 |
| Total | 100 | 100 | 100 | 100 | 100 |

TABLE 13

|  | Example 4 | Example 5 | Example 6 | Example 7 | Example 8 | Example 9 |
|---|---|---|---|---|---|---|
| Diclofenac Sodium | 1 | 1 | 1 | 1 | 1 | 1 |
| Hydrophobically-modified HPMC | 0.9 | 0.9 | 0.9 | 0.9 | 0.9 | 0.9 |
| HPC | 1 | 1 | 1 | 1 | 1 | 1 |
| Sucrose | 5 | — | — | — | — | — |
| Sorbitol | — | 5 | — | — | — | — |
| Macrogol 400 | — | — | 5 | — | — | — |
| Glycerin | — | — | — | 5 | — | — |
| Nikasol TS620 | — | — | — | — | 5 | — |
| POE (60) Hydrogenated Castor Oil | — | — | — | — | — | 5 |

TABLE 13-continued

|  | Example 4 | Example 5 | Example 6 | Example 7 | Example 8 | Example 9 |
|---|---|---|---|---|---|---|
| Propylene Glycol | 5 | 5 | 5 | 5 | 5 | 5 |
| Diisopropyl Adipate | 7 | 7 | 7 | 7 | 7 | 7 |
| POE (30) Behenyl Ether | 0.5 | 0.5 | 0.5 | 0.5 | 0.5 | 0.5 |
| Purified Water | Balance | Balance | Balance | Balance | Balance | Balance |
| Ethanol | Balance | Balance | Balance | Balance | Balance | Balance |
| Additional Components | 4.83 | 4.83 | 4.83 | 4.83 | 4.83 | 4.83 |
| Total | 100 | 100 | 100 | 100 | 100 | 100 |

Each of the thus obtained gel compositions was applied, in an amount of 0.3 g, onto the skin of a forearm of 5 subjects (healthy adults) in an application area of 30 cm$^2$, and about 3 hours later, a peeling state of a film (dried gel composition) was visually observed. Results of the observation were scored in accordance with the criteria described in Test 1, and an average thereof was calculated.

The results are shown in Table 14. The evaluation scores for scale-like shaped substances were 3.0 or less in Comparative Examples 4 to 8, but were 3.8 or more in Examples 4 to 9.

TABLE 14

|  | Comp. Example 4 | Comp. Example 5 | Comp. Example 6 | Comp. Example 7 | Comp. Example 8 |
|---|---|---|---|---|---|
| Score | 2.6 | 2.4 | 3.0 | 1.8 | 2.6 |

|  | Example 4 | Example 5 | Example 6 | Example 7 | Example 8 | Example 9 |
|---|---|---|---|---|---|---|
| Score | 3.8 | 4.2 | 4.6 | 4.2 | 4.8 | 4.8 |

Test 5: Evaluation of Spreadability

Respective components were mixed as shown in Table 15 to prepare gel compositions of Examples 10 to 15 and Comparative Example 9. Each numerical value shown in Table 15 is in "% by mass". Used hydrophobically-modified HPMC and Nikasol TS620 were the same as those described in Test 3. The term "Balance" shown in Table 15 means that purified water and ethanol in a mass ratio of 1:1 were added to make the mass of the whole composition 100. Additional Components shown in Table 15 refer to a physiologically active substance excluding diclofenac sodium, and another optional component.

TABLE 15

|  | Comp. Example 9 | Example 10 | Example 11 | Example 12 | Example 13 | Example 14 |
|---|---|---|---|---|---|---|
| Diclofenac Sodium | 1 | 1 | 1 | 1 | 1 | 1 |
| Hydrophobically-modified HPMC | 0 | 0.4 | 0 | 1 | 2 | 2 |
| HPC | 0 | 0.4 | 2 | 1 | 0 | 2 |
| Nikasol TS620 | 5 | 5 | 5 | 5 | 5 | 5 |
| Propylene Glycol | 5 | 5 | 5 | 5 | 5 | 5 |
| Diisopropyl Adipate | 7 | 7 | 7 | 7 | 7 | 7 |
| POE (30) Behenyl Ether | 0.5 | 0.5 | 0.5 | 0.5 | 0.5 | 0.5 |
| Purified Water | Balance | Balance | Balance | Balance | Balance | Balance |
| Ethanol | Balance | Balance | Balance | Balance | Balance | Balance |
| Additional Components | 4.83 | 4.83 | 4.83 | 4.83 | 4.83 | 4.83 |
| Total | 100 | 100 | 100 | 100 | 100 | 100 |

Each of the thus obtained gel compositions was rubbed, in an amount of 0.3 g, onto the skin of a forearm of 5 subjects (healthy adults) to be spread in an application area of 30 cm$^2$ for 10 to 30 seconds. Immediately after the application, the extent of falling of the composition was visually observed. Spreadability (easiness of spreading) and difficulty to fall of the gel composition were scored in accordance with the following criteria, and an average thereof was calculated.

<Evaluation Criteria of Spreadability>
1: very difficult to spread
2: difficult to spread
3: neither difficult nor easy to spread
4: easy to spread
5: very easy to spread <Evaluation Criteria of Falling>
1: vary easy to fall (The gel composition flowed, and half an amount thereof or more fell off from the skin within several seconds.)
2: easy to fall (The gel composition flowed, and less than half an amount thereof fell off from the skin within several seconds.)
3: neither difficult nor easy to fall (The gel composition did not fall off from the skin, but flowed downward on the skin within 10 seconds.)
4: difficult to fall (The gel composition did not fall off from the skin, but flowed downward on the skin after 10 seconds or more passed.)
5: very difficult to fall (The gel composition did not fall off from the skin, and did not flow on the skin.)

Results are shown in Table 16. In Examples 10 to 14, the spreadability (easiness of spreading) and/or difficulty to fall were excellent.

TABLE 16

|  | Comp. Example 9 | Example 10 | Example 11 | Example 12 | Example 13 | Example 14 |
| --- | --- | --- | --- | --- | --- | --- |
| Spreadability | 4.0 | 4.4 | 4.6 | 4.2 | 3.4 | 3.0 |
| Difficulty to Fall | 1.0 | 2.0 | 2.8 | 4.0 | 4.6 | 5.0 |

Gel compositions (Production Examples 1 to 6) respectively comprising, instead of diclofenac sodium, ketoprofen, indomethacin, felbinac, flurbiprofen, butenafine hydrochloride, and terbinafine hydrochloride were prepared in the same manner as in Example 1.

The invention claimed is:

1. An emulsified gel composition, comprising a physiologically active substance, water, a gelling agent, an anti-peeling agent, and a surfactant having an HLB value of 18 to 20, wherein the gelling agent is a nonionic water-soluble polymer, and the anti-peeling agent comprises a methyl acrylate/2-ethylhexyl acrylate copolymer.

2. The emulsified gel composition according to claim 1, wherein the physiologically active substance comprises diclofenac or a pharmacologically acceptable salt thereof.

3. The emulsified gel composition according to claim 1, wherein the nonionic water-soluble polymer comprises one or more compounds selected from the group consisting of hydroxypropyl cellulose and hydrophobically-modified hydroxypropyl methyl cellulose.

4. The emulsified gel composition according to claim 1, wherein the surfactant comprises at least one compound selected from the group consisting of polyoxyethylene behenyl ether, polyoxyethylene monostearyl ether, polyoxyethylene cetyl ether, and polyoxyethylene oleyl ether.

5. The emulsified gel composition according to claim 1, further comprising an aliphatic alcohol having 1 to 3 carbon atoms.

6. The emulsified gel composition according to claim 2, wherein the nonionic water-soluble polymer comprises one or more compounds selected from the group consisting of hydroxypropyl cellulose and hydrophobically-modified hydroxypropyl methyl cellulose.

7. The emulsified gel composition according to claim 2, wherein the surfactant comprises at least one compound selected from the group consisting of polyoxyethylene behenyl ether, polyoxyethylene monostearyl ether, polyoxyethylene cetyl ether, and polyoxyethylene oleyl ether.

8. The emulsified gel composition according to claim 3, wherein the surfactant comprises at least one compound selected from the group consisting of polyoxyethylene behenyl ether, polyoxyethylene monostearyl ether, polyoxyethylene cetyl ether, and polyoxyethylene oleyl ether.

9. The emulsified gel composition according to claim 2, further comprising an aliphatic alcohol having 1 to 3 carbon atoms.

10. The emulsified gel composition according to claim 3, further comprising an aliphatic alcohol having 1 to 3 carbon atoms.

11. The emulsified gel composition according to claim 4, further comprising an aliphatic alcohol having 1 to 3 carbon atoms.

* * * * *